United States Patent [19]

Mund et al.

[11] Patent Number: 4,603,704
[45] Date of Patent: Aug. 5, 1986

[54] ELECTRODE FOR MEDICAL APPLICATIONS

[75] Inventors: Konrad Mund, Uttenreuth; Helmut Freller, Roethenbach; Friedrich Hoerauf, Nuremberg, all of Fed. Rep. of Germany

[73] Assignee: Siemens Aktiengesellschaft, Berlin & Munich, Fed. Rep. of Germany

[21] Appl. No.: 569,832

[22] Filed: Jan. 11, 1984

[30] Foreign Application Priority Data

Jan. 11, 1983 [DE] Fed. Rep. of Germany ....... 3300668

[51] Int. Cl.$^4$ .............................................. A61N 1/04
[52] U.S. Cl. ................................. 128/784; 128/419 P
[58] Field of Search ..................... 128/419 P, 784–786

[56] References Cited

U.S. PATENT DOCUMENTS

| 4,033,357 | 7/1977 | Helland et al. | 128/785 |
| 4,281,669 | 8/1981 | MacGregor | 128/784 |
| 4,440,178 | 4/1964 | Bussard et al. | 128/784 |

FOREIGN PATENT DOCUMENTS 0054781  6/1982  European Pat. Off. ............ 128/784

Primary Examiner—William E. Kamm
Attorney, Agent, or Firm—Hill, Van Santen, Steadman & Simpson

[57] ABSTRACT

In order to expand the availability of effective and usable electrodes for medical applications, an electrode is proposed which is comprised of an electrically conductive carrier material and of a porous layer in its active region which is composed of a carbide, nitride or carbonitride of one of the metals titanium, vanadium, zirconium, niobium, molybdenum, hafnium, tantalum or tungsten.

16 Claims, 2 Drawing Figures

ELECTRODE FOR MEDICAL APPLICATIONS

CROSS-REFERENCE TO RELATED APPLICATIONS

Reference is made pursuant to a copending application U.S. Ser. No. 569,980 filed Jan. 11, 1984 in the names of Lars Botvidsson and Konrad Mund, entitled "Bipolar Electrode for Medical Applications" and to a copending application U.S. Ser. No. 569,979 filed Jan. 11, 1984 in the names of Hakan Elmqvist and Konrad Mund, entitled "Heart Pacemaker System". German published application Nos. 33 00 694 and 33 00 672.

BACKGROUND OF THE INVENTION

The invention relates to an electrode for medical applications, particularly an implantable stimulation electrode.

Electrodes for medical applications are employed in the form of effectors and sensors. What is meant by effectors are electrodes with which a stimulating effect is exerted. Sensors are electrodes used for measuring. Examples of effectors are stimulation electrodes for heart pacemakers as well as electrodes for the stimulation of nerves and muscles. Particularly coming into consideration as sensors are microelectrodes for potential pick-up as well as EEG and ECG electrodes, i.e. electrodes for sensing brain and heart currents, respectively.

In most cases, implantable stimulation or stimulating electrodes, for example for heart pacemakers, consist of an electrode shank having an insulated cable lead and of an electrode head for the transmission of the stimulation pulses, i.e. the active or effective area of the electrode. Essentially two demands are made of such electrodes:

1. The electrode material must be compatible with the body, i.e. the formation of connective tissue layers should be very low if it is not suppressed altogether; in any case, the thickness should remain below one hundred microns (100 $\mu$m). The stimulation threshold, further, should remain largely constant.

2. A high double layer capacitance should form at the phase boundary electrode/bodily fluid, so that the polarization rise during the stimulation pulses (0.5 through 1 ms, 1 Hz, 10 mA, 10 mm$^2$) remains less than 0.1 V.

The high double layer capacitance that is required has a beneficial effect in the case of stimulation electrodes and generally in the case of effectors as well because, as a result of the impressed current, only slight potential changes occur, electrochemical reactions with the bodily fluid are largely suppressed and the energy outlay is slight. In the case of sensors in which only a small measurement current flows, a high capacitance of the electrodes relaxes the demands that are made of the input impedance of amplifiers; noise is also reduced.

The demands cited above are particularly well met by electrodes wherein the electrode head, i.e. the active region in general, consists of glassy carbon. The high double layer capacitance of up to 0.1 F/cm$^2$ ($\nu = 1$ Hz) is achieved by means of an activation of the surface of the glassy carbon, whereby a thin, firmly adhering layer of activated carbon is obtained, i.e. a surface with a microporous structure.

Activated glassy carbon thus repesents an electrode material having high capacitance that, beyond this, also exhibits good bodily compatibility and can therefore replace the metallic materials such as platinum/iridium for stimulation electrodes, platinum and tungsten for microelectrodes and silver/silver chloride for ECG electrodes which effect a degeneration of the adjacent tissue. Given glassy carbon, on the other hand, problems arise with respect to the mechanical processing (during manufacture) and the contacting, this in turn not being the case when metal electrodes are used.

SUMMARY OF THE INVENTION

A principal object of the invention is to avoid the problems regarding the electrode material hitherto occurring in electrodes for medical applications and to thus expand the availability of effective and usable electrodes.

This is inventively achieved in that the electrode is comprised of an electrically conductive carrier material and has a porous layer consisting of a carbide, a nitride or a carbonitride of at least one of the metals titanium, vanadium, zirconium, niobium, molybdenum, hafnium, tantalum or tungsten in its active region. The active region should thereby at least partially exhibit such a porous layer.

The metals forming the carbides, nitrides and carbonitrides are all elements of the fourth through sixth sub-group of the periodic system and are thus included among the so-called transition metals. TiC, TiN, ZrC, ZrN, TaC and TaN are, for example, carbides (MeC) and nitrides (MeN) of the said type (Me=metal). It is thereby essentially a matter of the stoichiometric compounds but deviations from the stoichiometric ratio can be present. The carbonitrides exhibit the composition $MeC_xN_{1-x}$, whereby x can assume a value between 0 and 1; for example, let the compound $TiC_{0.5}N_{0.5}$ be cited in this regard. In all instances, "mixed" compounds can also exist, i.e. Me can also stand for several metals in various proportions to each other; the carbide (W,Ti)C is an example of such a compound. Beyond this, the said compounds can also be utilized in the form of mixtures.

Given the inventive electrode, the porous layer of metal carbide, metal nitride or metal carbonitride which has good electrical conductivity generally exhibits a thickness between one micron and one hundred microns (1 and 100 $\mu$m); the layer thickness preferably lies between five microns and fifty microns (5 and 50 $\mu$m). Double layer capacitances of 10 mF/cm$^2$ up to 100 mF/cm$^2$ thereby result. The inventive electrodes are comparable to electrodes of activated glassy carbon due to this high capacitance and the low polarization deriving therefrom as well as due to the good bodily compatibility which results in stability of the stimulation threshold. With respect to the contacting, the inventive electrodes exhibit advantages over glassy carbon electrodes since they consist of electrically conductive material.

The individual stimulation pulses in heart pacemakers last 0.5 through 1 ms. That means that the current must largely penetrate into the porous layer during this brief time in order to exploit the capacitance to the highest degree possible. This goal, however, can only be achieved when the ohmic resistance of the electrolyte in the pore system is sufficiently low, as is the case given the inventive electrode. Thereby characteristic is the product of volume-associated capacitance c, resistivity $\rho$ of the eleotrolyte in the pores and the square of the thickness d of the porous layer. The limiting condition reads: $2\pi \cdot \nu \cdot c \cdot \rho \cdot d^2 < 1$.

The porous carbide, nitride or carbonitride layer is situated on an electrically conductive carrier material. This carrier material must be essentially blood and tissue compatible, i.e. compatible to the body. Metals and metal alloys such as Elgiloy and stainless steel (so-called VA steel) therefore come into consideration as the carrier material given the inventive electrode. Platinum and titanium are preferably employed; other precious metals can also be additionally employed. Beyond this, the carrier material can also consist, for example, of a synthetic coated with metal. Given the inventive electrode, at least the active region exhibits the thin, porous layer. Other (metallic) regions of the electrode can also be provided with such a layer under given conditions.

Given the inventive electrode, a dense nonporous sealing layer consisting of the same material as the porous layer can be situated between the carrier material and the thin, porous layer. With, for example, titanium as the electrode material, a dense nonporous titanium nitride layer can first be disposed thereon, followed by a porous titanium nitride layer. The formation of material-associated differential potentials can be prevented by means of the additional, dense nonporous layer. Beyond this, the demand that the carrier material must be physically compatible is thereby also eliminated. The thickness of the dense, i.e. nonporous sealing layer preferably amounts to between two and ten microns (2 and 10 $\mu$m).

The thin, porous layers are preferably applied to the carrier material such as titanium and platinum serving as substrate by means of reactive ion plating, i.e. by means of physical vapor deposition. With, for example, an electron beam evaporator, the metal for the porous layer is evaporated in an atmosphere containing nitrogen and/or methane (with, for example, argon present as an inert gas), being evaporated to this end from a supply of the metal forming the nitride, carbide or, respectively, carbonitride, and the corresponding metal compound, i.e. the carbide, nitride or carbonitride, is then deposited on the substrate as a thin layer. The $N_2$ or, respectively, $CH_4$ partial pressure thereby generally amounts to between $5 \cdot 10^{-3}$ and $10^{-1}$ mbar. The reactive ion plating can, however, also ensue with a magnetron sputter source, whereby the reaction gas pressures for $N_2$ or, respectively, $CH_4$ lie about one order of magnitude lower ($4 \cdot 10^{-4}$ through $1 \cdot 10^{-2}$ mbar).

Given the manufacture of an electrode wherein a corresponding, dense nonporous sealing layer is situated between the carrier material and the porous layer, one advantageously proceeds such that the $N_2$ and/or $CH_4$ partial pressure is slowly increased during the coating of the substrate, namely, for example, from a value between about $2 \cdot 10^{-3}$ and $8 \cdot 10^{-3}$ mbar to a value between $5 \cdot 10^{-3}$ and $10^{-1}$ mbar. Given such a procedure, namely, the dense i.e. nonporous sealing layer is first formed on the substrate and the corresponding, porous layer is formed thereafter. In addition to the $N_2$ or, respectively, $CH_4$ partial pressure, the formation of dense (nonporous) or, respectively, porous layers also depends, moreover, on the ion current of the gas discharge that is ignited between the substrate and the electron beam evaporator.

The inventive electrode is particularly suited for the following applications:

Stimulation electrodes

The pore system of the porous layer provides a high double layer capacitance which is aimed at, for example, use as stimulation electrodes of implantable heart pacemakers in order to keep the energy outlay low.

Microelectrodes

In the simplest case, these are thin wires having a diameter of less than fifty microns (50 $\mu$m) that are pointed. Such electrodes are advantageously essentially completely provided with a thin porous layer. The high double layer capacitance is then formed at the (active) electrode tip when immersed into the electrolyte, whereas the pores of the porous layer along the electrode shank, i.e. along the wire, represent a good bonding base for the insulation.

EEG and ECG electrodes

The high attainable capacitance is also here advantageous. But it is also significant that the porous layer is anchored to the carrier material in an abrasion-proof manner and the electrode—after appropriate cleaning—can thus be repeatedly employed.

Cooperating electrodes

It is advantageous when, for example, the stimulation and cooperating electrode consist of the same material because potential differences dependent on material cannot occur then.

DETAILED DESCRIPTION

Figure 1:
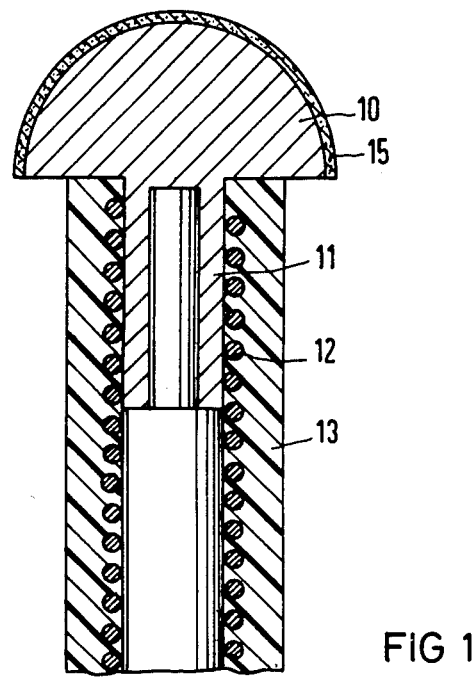
FIG. 1 is a partial longitudinal sectional view for illustrating an electrode for medical applications with a porous layer having characteristics in accordance with the present invention.

FIG. 1 shows an electrode for medical applications, comprising so far as relevant an electrode head 10 having a stem 11 which is in electrical contact with a contacting helix 12, the helix 12 being covered by a suitable synthetic coating 13.

In accordance with the present invention, the electrode head serves as an electrically conductive carrier material in electrical connection with helix 12 and supports a porous layer 15 comprised of one or more compounds each consisting of a carbide, nitride or carbonitride of at least one of the metals titanium, vanadium, zirconium, niobium, molybdenum, hafnium, tantalum or tungsten. The porous layer 15 has a layer thickness between one micrometer (one micron) and one hundred micrometers, and preferably between about five micrometers and about fifty micrometers. By way of example the electrode head 10 and stem 11 may be of titanium or platinum, and the helix 12 may be of Elgiloy.

As explained in detail hereafter, in a further embodiment of the invention, the porous layer may be applied over a dense nonporous sealing layer of the same material as the porous layer. The dense nonporous sealing layer together with the synthetic coating 13 may completely cover the metallic material of head 10 and stem 11, so that this metallic material is not exposed to bodily fluids when the electrode is implanted. The dense sealing layer may have a layer thickness between about two micrometers and about ten micrometers. Bodily fluids may penetrate the porous layer to a depth between about one micrometer and about one hundred micrometers so as to be separated from the metallic carrier material only by the sealing layer; thus the separation between the bodily fluid and the metallic carrier material is in the range from about two micrometers to about ten micrometers.

Figure 2:
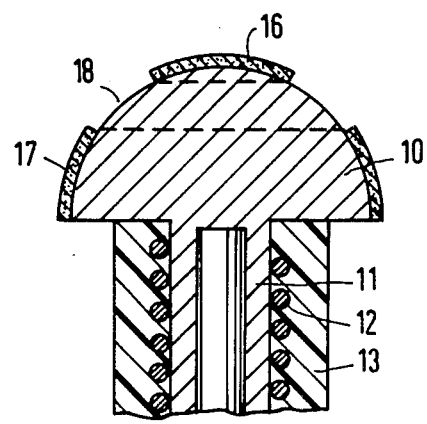
FIG. 2 is a view similar to FIG. 1, the electrode having a plurality of active regions each formed by a porous layer with a composition and other characteristics in accordance with the present invention.

FIG. 2 illustrates the same basic electrode configuration as FIG. 1, and corresponding reference numerals have been applied to the electrode head, electrode stem, the contacting helix and the synthetic coating. In FIG. 2 the electrode head 10 is shown as having spaced porous layers 16 and 17 which are separated from each other by region 18 without a porous layer. The porous layers 16 and 17 have the same composition and layer thickness as described for porous layer 15 of FIG. 1. The region or regions such as 18 may expose the metallic material of the electrode head 10 to bodily fluids where the electrode head is formed of a compatible material.

As described with reference to FIG. 1, the metallic carrier material of electrode head 10 of FIG. 2, in a further embodiment, may have a dense nonporous sealing layer which together with the synthetic coating 13 completely isolates the metallic material of electrode head 10 and stem 11 from bodily fluids when the electrode is implanted.

By way of example, the electrodes of FIGS. 1 and 2 may serve as implantable stimulation electrodes and provide a double layer capacitance measured with a pulse repetition rate of one hertz as explained herein, which lies in the range from about ten millifarads per centimeter squared to about one hundred millifarads per centimeter squared. The method of manufacture and detailed characteristics of the porous layers 15, 16 and 17 of FIGS. 1 and 2 may be as described in any of the following examples, and the electrode systems utilizing of the electrodes described in this section may provide the features and advantages as set forth herein in the section headed Summary of the Invention.

The invention shall be explained in greater detail with reference to examples.

In the investigations described below, electrodes whose porous layer exhibited a thickness of approximately thirty microns (30 μm) were respectively employed.

The structure of the porous layers depends on the manufacturing conditions. A needle-like structure was obtained given a $N_2$ pressure of one millibar wherein the needles have a diameter of about one-half micron (0.5 μm). The layer has a volume porosity of forty percent (40%).

Titanium nitride-coated titanium sheets, for example, served for the determination of the electrochemical properties, having been investigated in a half cell arrangement with 0.15 M NaCl as the electrolyte. A smooth platinum sheet served as cooperating electrode; an AgCl electrode was employed as the reference electrode. The electrodes were connected to a potentiostat and the potential values were converted and related to the potential of the reversible hydrogen electrode ($H_2$ electrode). The electrodes thereby set a potential of $\phi/H_2\,_{rev} = 0.89$ V. (The specification $\phi/H_2\,_{rev}$ denotes a potential referred to the reverible hydrogen electrode.) Under potentio-dynamic load, with a voltage rate of change of ten millivolts per second (10 mV/$_s$), one observed a constant current in the center of the interval $0 \leq \phi/H_2\,_{rev} \leq 1$ V. Therefrom a double layer capacitance of 68 mF/cm$^2$ occurred at the beginning of the load, and this did not change over a load duration of eighty-eight hours (88 h). The investigations showed that no corrosion occurred up to a potential of 1.1 V; the electrodes are thus sufficiently stable.

In order to investigate the bodily compatibility of the electrodes, titanium sheets having a black, porous TiN layer as well as titanium sheets having a yellow, dense nonporous sealing TiN layer were implanted into the thigh muscle of cats (wafers having a diameter of 10 mm). After an implantation duration of 5 weeks, there were no differences with respect to the connective tissue growth between the various specimens, i.e. given passively implanted electrodes. Beyond this, the thickness of the connective tissue layer in all specimens amounted to less than sixty microns (60 μm), i.e. there is nearly ideal tissue compatibility.

Electrode heads in the form of hemispheres having a diameter of 2 mm were manufactured from Ti wire. These hemispheres were coated with porous titanium nitride, the electrode shank was contacted with an Elgiloy helix. (Elgiloy is a corrosion resistant stainless steel having the following components: Co, Cr, Ni, Fe, Mo, Mn, C and Be.) Given electrodes intended for implantation, moreover, the electrode shank is always coated with a suitable material such as a synthetic so that no problems with respect to the physical compatibility thereby derive. The double layer capacitance of such stimulation electrodes—which was identified potentiostatically from impedance measurements—derived at 21.5 mF/cm$^2$ in 0.15 M NaCl given $\nu = 1$ Hz. The value could be increased to 48 mF/cm$^2$ given further specimens of stimulation electrodes Because of the high porosity of the layers, however, this capacitance is available up to frequencies of 10 Hz. The capacitance decreases with increases of frequency and reaches a value of 8 mF/cm$^2$ at a frequency $\nu = 100$ Hz. This drop is caused by the porous structure of the layer and the penetration depth of the current decreases with increasing frequency as a consequence of the electrolyte resistance. The capacitance measurements were conducted at an impedance test location, whereby a potentiostat was coupled to a frequency response analyzer. The imaginary component of the impedance was interpreted.

In in vitro experiments, stimulation electrodes were loaded together with a heart pacemaker at a voltage of 5 V, a pulse duration of 0.75 ms and an electrolyte temperature of 40° C. over a time span of 4,500 hours. A capacitance decrease of 20% was observed over the first 1,000 hours but the value of the capacitance then stabilized.

A capacitance of 10.5 mF/cm$^2$ (given $\nu = 1$ Hz) was identified in the animal testing (implantation of the stimulation electrode in the thigh muscle of cats). Conditioned by the body fluid, this value lies approximately 50% lower than the value of the in vitro measurements (NaCl). But what is thereby significant is that the capacitance values did not change even after an implantation duration of 42 days. A thin connective tissue layer having a thickness between thirty and sixty microns (30 and 60 μm) formed during this time, this again demonstrating the good tissue compatibility.

Stimulation electrodes of the type illustrated in FIG. 1 were also implanted in dogs' hearts. After 6 weeks, analysis showed that the electrodes were surrounded with connecting tissue having a thickness of less than 100 microns. The employed electrode material is thus bodily compatible.

The inventive electrode can also exhibit a plurality of regions that are provided with a porous layer. These regions then alternate with regions that exhibit no porous layer. Having the current density rise in specific directions can be achieved by means of such a geometrical disposition.

It will be apparent that many modifications and variations may be made without departing from the scope of the teachings and concepts of the present invention.

We claim as our invention:

1. An electrode for medical applications comprising an electrically conductive carrier material and a porous layer defining an active region, said porous layer being of a material comprised of at least one compound selected from the group consisting of a carbide, nitride or carbonitride of at least one of the metals titanium, vanadium, zirconium, niobium, molybdenum, hafnium, tantalum or tungsten, said porous layer having a layer thickness between one micron and one hundred microns.

2. An electrode as claimed in claim 1, wherein a dense nonporous layer of a material corresponding to the material of the porous layer is situated between the carrier material and the porous layer.

3. An electrode as claimed in claim 2, wherein the dense layer has a layer thickness between two and ten microns.

4. An electrode as claimed in claim 1, with said electrode having a plurality of active regions each having a porous layer comprised of at least one of said compounds, the regions having said porous layer separated from one another by regions without a porous layer.

5. An electrode as claimed in claim 1, wherein the carrier material is titanium.

6. An electrode as claimed in claim 1, wherein the carrier material is platinum.

7. An electrode as claimed in claim 1, wherein the porous layer has a layer thickness between about five microns and about fifty microns.

8. An electrode as claimed in claim 7, wherein the carrier material is titanium.

9. An electrode as claimed in claim 7, wherein the carrier material is platinum.

10. An electrode as claimed in claim 7, wherein a dense nonporous sealing layer comprised of at least said one of said compounds in the porous layer is disposed between the carrier material and the porous layer.

11. An electrode as claimed in claim 10, wherein the dense nonporous sealing layer has a layer thickness between two and ten microns.

12. An electrode system for medical applications comprising an implantable stimulation electrode, said implantable stimulation electrode comprising an electrically conductive carrier material and at least one active region formed of a porous exposed layer exposed to bodily fluids, said porous exposed layer being of a material formed of at least one compound having the formula MeX, where Me is at least one of the metals selected from the group consisting essentially of titanium, vanadium, zirconium, niobium, molybdenum, hafnium, tantalum and tungsten, and where X is selected from the group consisting essentially of at least one of carbon and nitrogen, said porous exposed layer having a layer thickness permeable to bodily fluids which is between about one micron and about one hundred microns in depth.

13. An electrode system according to claim 12, with said porous exposed layer of said implantable stimulation electrode having a layer thickness about five microns and about fifty microns.

14. An electrode system according to claim 12, with said electrically conductive carrier material having a dense nonporous sealing layer isolating said carrier material from bodily fluids, said dense nonporous sealing layer being of a material corresponding to the material of said porous exposed layer, said porous exposed layer being applied on said dense nonporous sealing layer.

15. An electrode system according to claim 14, wherein said dense nonporous sealing layer has a layer thickness between two and ten microns.

16. An electrode system according to claim 12, with said implantable stimulation electrode having a plurality of separate active regions each formed with a porous exposed layer of said material and having said layer thickness, and said porous exposed layers being separated from one another by regions without a porous exposed layer.

* * * * *